US00PP19412P2

(12) United States Plant Patent
Jensen

(10) Patent No.: US PP19,412 P2
(45) Date of Patent: Nov. 4, 2008

(54) ***CAMPANULA* PLANT NAMED 'PKMTAK1'**

(50) Latin Name: *Campanula takesimana*
Varietal Denomination: PKMTAK1

(75) Inventor: Gert Kim Jensen, Norge (DK)

(73) Assignee: Gartneriet Pkm A/S, Odense N (DK)

( * ) Notice: Subject to any disclaimer, the term of this patent is extended or adjusted under 35 U.S.C. 154(b) by 0 days.

(21) Appl. No.: 11/907,440

(22) Filed: Oct. 12, 2007

(30) Foreign Application Priority Data

Jun. 11, 2007 (EM) ..... 2007/1295

(51) Int. Cl.
*A01H 5/00* (2006.01)

(52) U.S. Cl. ..... Plt./414

(58) Field of Classification Search ..... Plt./214, Plt./263

See application file for complete search history.

*Primary Examiner*—Annette H Para
*Assistant Examiner*—S. B. McCormick-Ewoldt
(74) *Attorney, Agent, or Firm*—Foley & Lardner LLP

(57) ABSTRACT

A new and distinct cultivar of *Campanula* plant named 'PKMTAK1', characterized by having compact plant habit; dense and bushy plant form, mainly due to short, upright and stiff stems; vigorous growth habit, but with less need for chemical growth retardation; small leaf size of apical and basal leaves; and deep rose colored flowers.

8 Drawing Sheets

Latin name of genus and species of the plant claimed: *Campanula takesimana.*
Variety denomination: 'PKMTAK1'.

BACKGROUND OF THE INVENTION

The present invention relates to a new and distinct cultivar of *Campanula* plant, botanically known as *Campanula takesimana,* commonly known as Korean Bellflower, and hereinafter referred to by the name 'PKMTAK1'.

The new *Campanula* 'PKMTAK1' is a product of a planned breeding program conducted by the inventor, Gert K. Jensen, in Søhus, Denmark. The objective of the breeding program is to develop a new *Campanula* cultivar with compact plant form and rose colored flowers.

The new *Campanula* cultivar originated from a cross made in a controlled breeding program by the inventor in 2000 in Søhus, Denmark. The female or seed parent is an unpatented, proprietary cultivar selected from the internal breeding line of *Campanula takesimana* designated by internal no. 21.00.2146. The male or pollen parent is an unpatented, proprietary cultivar selected from the internal breeding line of *Campanula takesimana* designated by internal no. 21.99.2145. The new *Campanula* 'PKMTAK1' was discovered and selected by the inventor as a single flowering plant within the progeny of the stated cross in March of 2000 in a controlled environment in Søhus, Denmark. The inventor selected 'PKMTAK1' on the basis of its compact plant form and deep rose colored flowers.

Asexual reproduction of the new *Campanula* cultivar by terminal cuttings was first performed in March of 2001 in Søhus, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMTAK1'. These characteristics in combination distinguish 'PKMTAK1' as a new and distinct cultivar:

1. Compact plant habit;
2. Dense and bushy plant form, mainly due to short, upright and stiff stems;
3. Vigorous growth habit, but with less need for chemical growth retardation;
4. Small leaf size of apical and basal leaves; and
5. Deep rose-colored flowers.

Plants of the instant cultivar 'PKMTAK1' differ primarily from plants of the unpatented, proprietary parental cultivars selected from the internal breeding lines of *Campanula takesimana* designated by internal nos. 21.00.2146 (female or seed parent) and 21.99.2145 (male or pollen parent) by the following characteristics:

1. Plants of 'PKMTAK1' are more compact and produce smaller flowers than plants of the internal breeding line of *Campanula takesimana* designated by internal no. 21.00.2146 (female or seed parent); and
2. Plants of 'PKMTAK1' are more vigorous in growth and produce large flowers than plants of the internal breeding line of *Campanula takesimana* designated by internal no. 21.99.2145 (male or pollen parent).

Side-by-side comparisons were conducted by the inventor in Stige, Denmark, among plants of the instant cultivar 'PKMTAK1' and plants of the most similar commercial cultivar, *Campanula takesimana.* 'Elizabeth' (unpatented). Plants of 'PKMTAK1' differ from plants of *Campanula takesimana.* 'Elizabeth' in the following characteristics:

1. Plants of 'PKMTAK1' are shorter and more compact in shape than plants of *Campanula takesimana* 'Elizabeth';
2. Plants of 'PKMTAK1' have shorter internodes, petioles, and leaves than plants of *Campanula takesimana* 'Elizabeth';
3. Plants of 'PKMTAK1' have shorter peduncles than plants of *Campanula takesimana* 'Elizabeth'; and 4. Plants of 'PKMTAK1' produce flowers with a deeper rose color than flowers produced by plants of *Campanula takesimana* 'Elizabeth'.

BRIEF DESCRIPTION OF THE PHOTOGRAPHS

The accompanying colored photographs illustrate the overall appearance of the new *Campanula* 'PKMTAK1', showing the colors as true as it is reasonably possible to obtain in colored reproductions of this type. Colors in the photographs may differ slightly from the color values cited in the detailed botanical description, which more accurately describe the actual colors of 'PKMTAK1'.

DETAILED BOTANICAL DESCRIPTION

Figure 1:
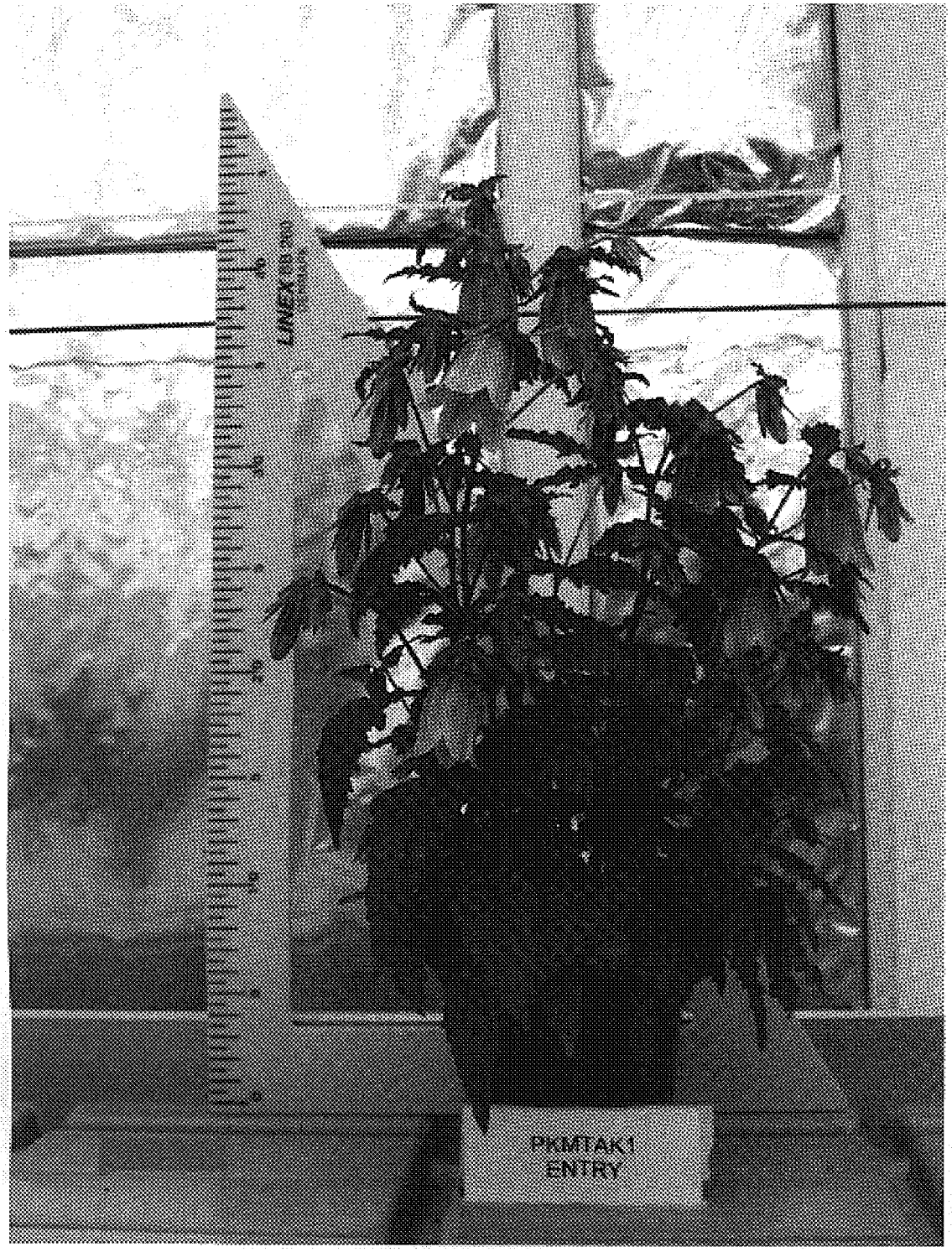
FIG. 1 shows a side perspective view of a typical flowering plant of 'PKMTAK1', as grown in a 10.5 cm pot at about 10 months of age after cutting.
Figure 2:
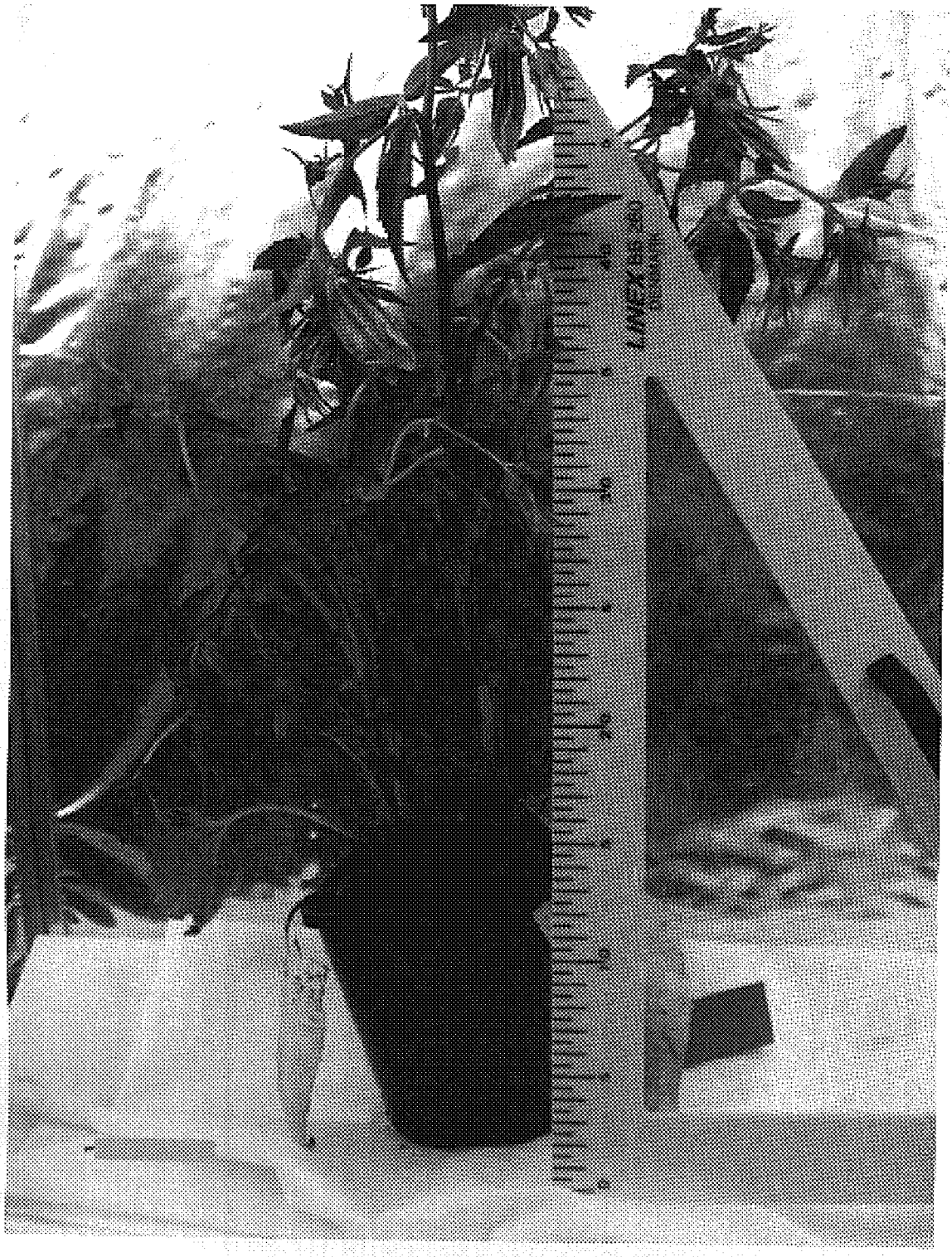
FIG. 2 shows a close-up side perspective view of a typical flowering plant of 'PKMTAK1', as grown in a 10.5 cm pot at about 10 months of age after cutting.
Figure 3:
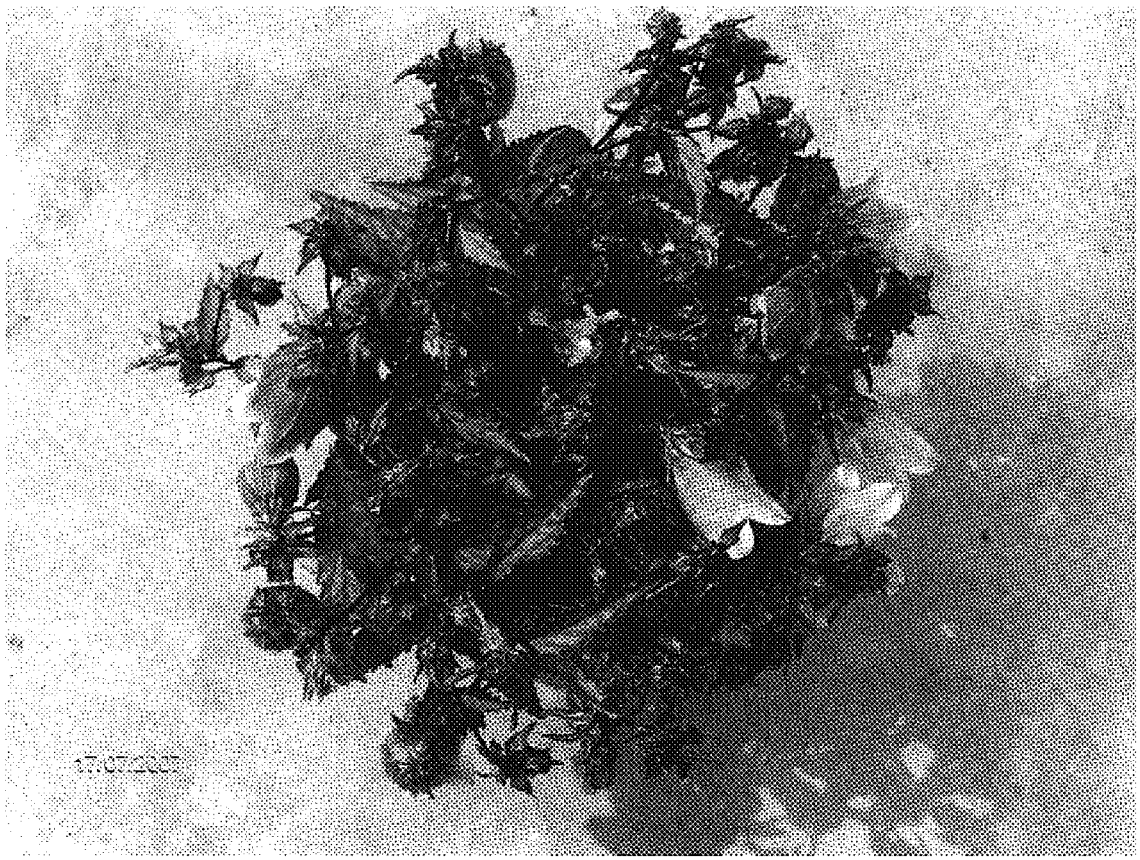
FIG. 3 shows a top perspective view of a typical flowering plant of 'PKMTAK1', as grown in a 10.5 cm pot at about 10 months of age after cutting.
Figure 4:
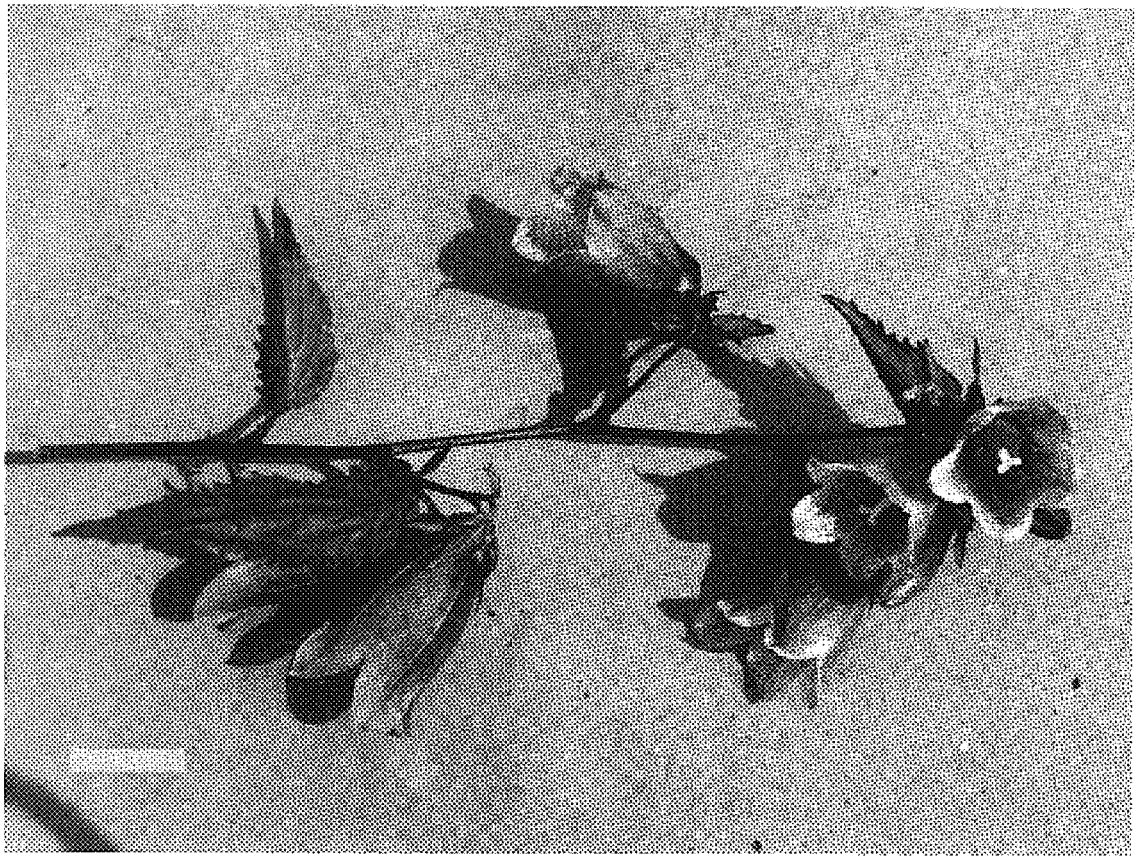
FIG. 4 shows a close-up view of a typical flowering raceme and leaves of 'PKMTAK1' at about 10 months of age after cutting.
Figure 5:
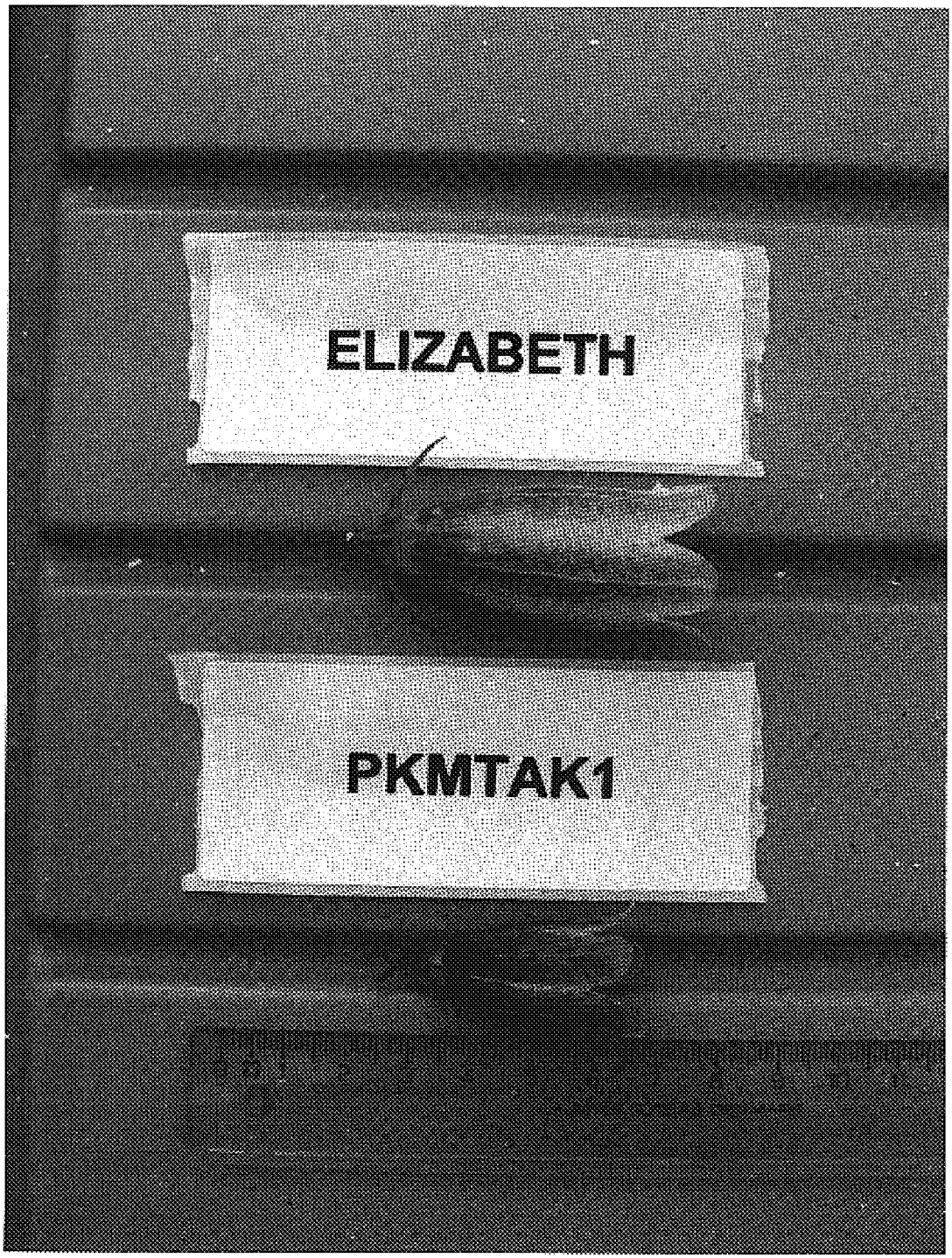
FIG. 5 shows a comparison perspective of a close-up view of a typical flower of the comparison cultivar 'Elizabeth' to the new cultivar 'PKMTAK1', at about 10 months of age after cutting.
Figure 6:
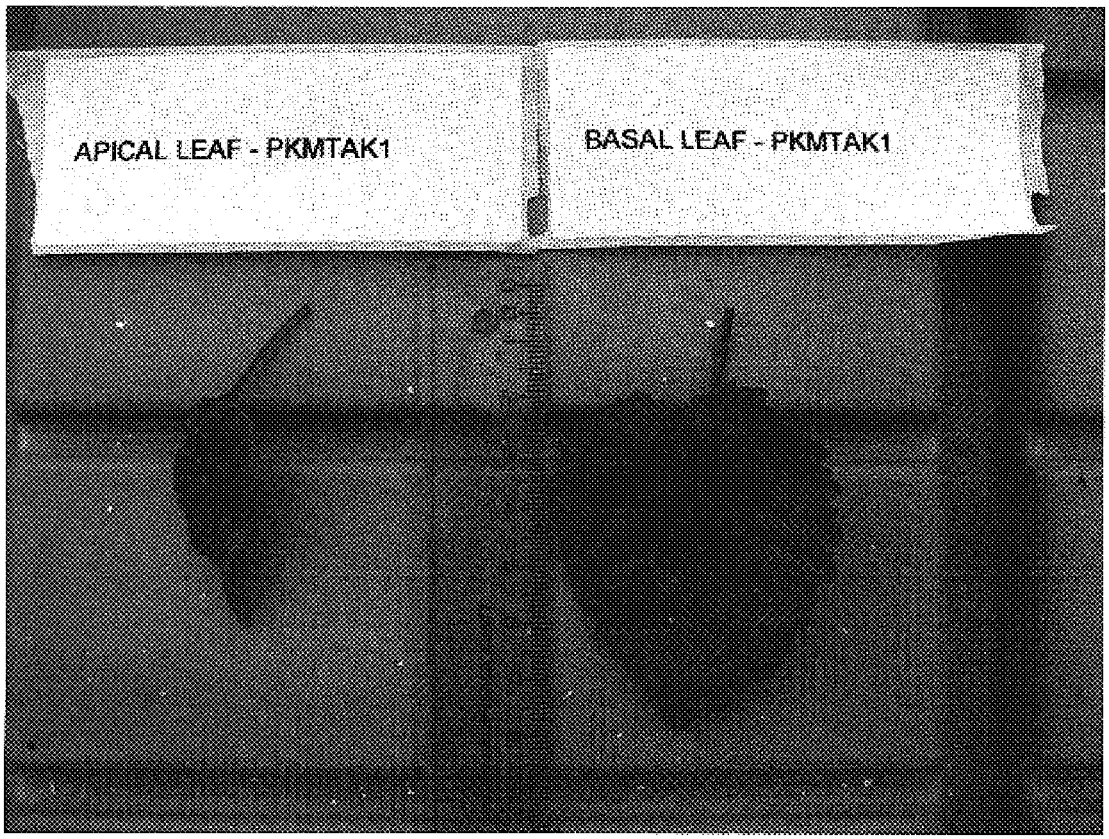
FIG. 6 shows a comparison perspective of a close-up view of a mature, apical leaf and a mature, basal leaf of the new cultivar 'PKMTAK1', at about 10 months of age after cutting.
Figure 7:
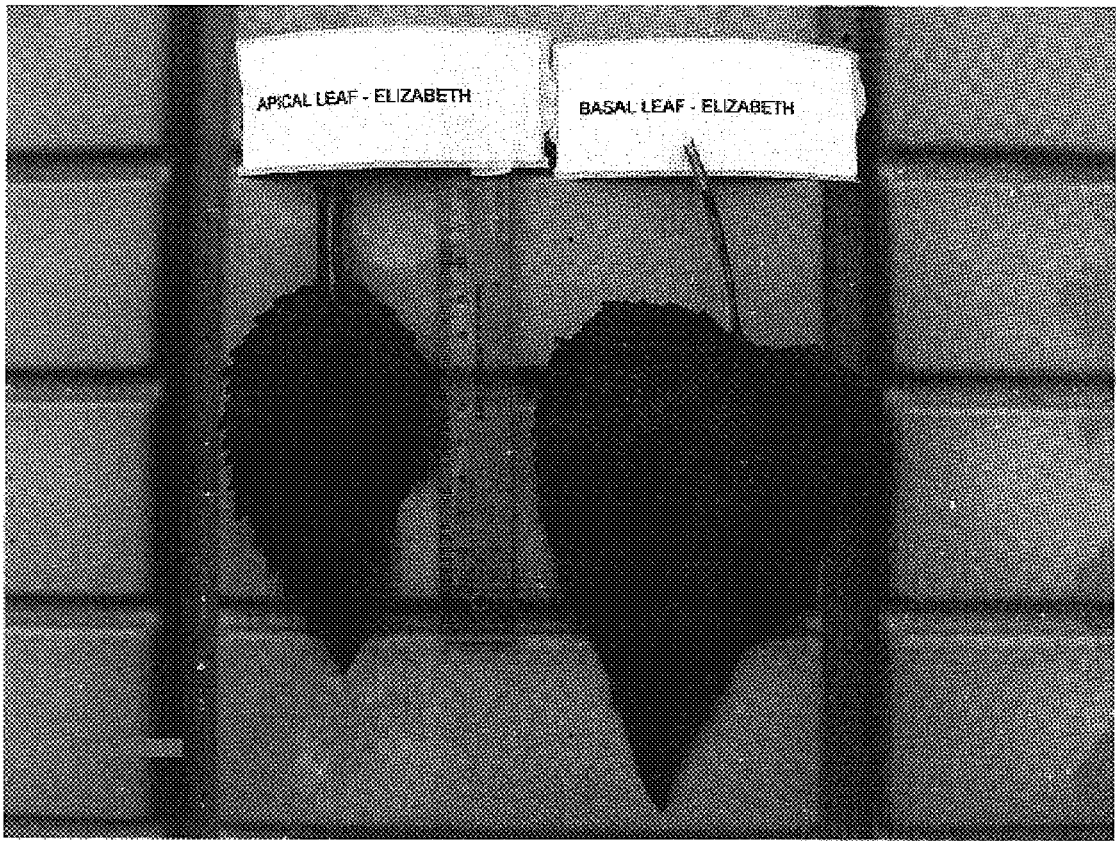
FIG. 7 shows a comparison perspective of close-up view of a mature, apical leaf and a mature, basal leaf of the comparison cultivar 'Elizabeth', at about 10 months of age after cutting.
Figure 8:
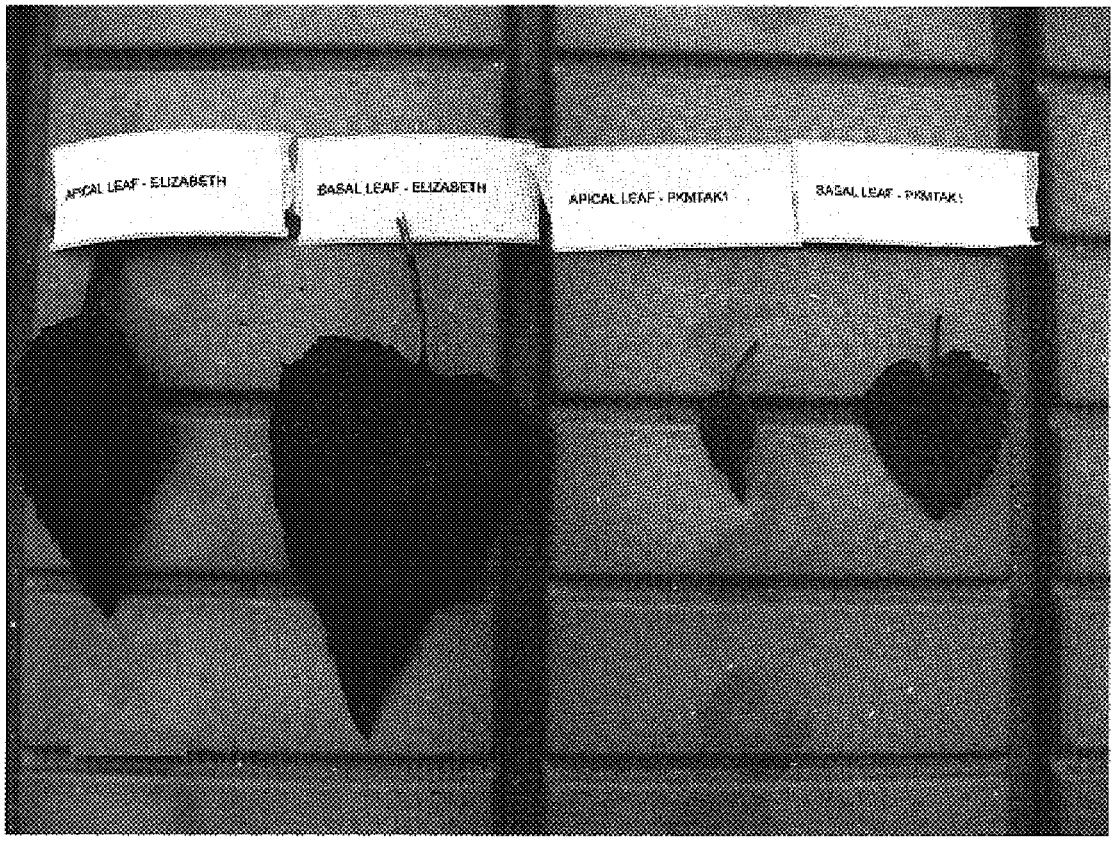
FIG. 8 show a comparison perspective of close-up view of a mature, apical leaf and a mature, basal leaf of the comparison cultivar 'Elizabeth' at about 10 months of age after cutting to a mature, apical leaf and a mature, basal leaf of the new cultivar 'PKMTAK1' at about 10 months of age after cutting.

The new *Campanula* 'PKMTAK1' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* 'PKMTAK1' as grown in a heated and lighted, glass-covered greenhouse in Søhus, Denmark, under conditions which closely approximate those generally used in commercial practices where day temperatures in the greenhouse range from 18–22° C. and the night temperature averages 16° C. Ambient light levels used while growing plants of 'PKMTAK1' are +55 $Wm^2$. Plants of 'PKMTAK1' are grown with 16 hour long day photoperiodic treatments. The growth regulator Daminozide is used. Prior to growing plant of 'PKMTAK1' in a heated and lighted, glass-covered greenhouse, propagation and growing of the seedling of 'PKMTAK1' occurs under 10 hour short day photoperiodic treatments. In addition, the plants of 'PKMTAK1' are first grown outdoors during the winter before being grown indoors in a heated and lighted, glass-covered greenhouse.

The age of the 'PKMTAK1' plants described in about 10 months after cutting and are grown in 10.5 cm pots. The photographs and descriptions were taken during the winter season when day temperatures in a glass-covered greenhouse range from 18–22° C. and when night temperatures in a glass-covered greenhouse average 16° C.

Color references are made to The Royal Horticultural Society Colour Chart (R.H.S.), $4^{th}$ edition, except where general colors of ordinary significance are used.

Classification:

*Botanical.*—*Campanula takesimana.*

Parentage:

*Female or seed parent.*—Unpatented, proprietary cultivar selected from the internal breeding line of *Campanula takesimana* designated by internal no. 21.00.2146.

*Male or pollen parent.*—Unpatented, proprietary cultivar selected from the internal breeding line of *Campanula takesimana* designated by internal no. 21.99.2145.

Propagation:

*Type cutting.*—Terminal vegetative cuttings.

*Time to initiate roots.*—About 12 to 15 days at 18 to 21° C. in tunnels in a greenhouse.

*Roots description.*—Fine, well branched.

*Root structure.*—Fibrous with many rhizomes.

*Root color.*—RHS 156B, gray-white.

Plant description:

*Form.*—Perennial, herbaceous plant with upright, compact plant habit. Produced as a potted plant. Campanulate flowers in racemes. Freely branching from rhizomes.

*Crop time.*—After rooting, about 9 to 11 months are required to produce finished flowering plants in 10.5 cm pots.

*Vigor.*—Vigorous growth rate.

*Plant height* (*from pot rim to top of plant plane*).—About 35 to 45 cm.

*Plant spread* (*width*).—About 30 cm.

*Lateral branches.*—Habit: Basal shoots from rhizomes. Quantity: About 15 to 20 per plant. Leaves per Lateral Branch: About 5 to 7. Length (including flowers): Ranges from 10 cm to 45 cm. Diameter: About 1 mm. Internode Length: About 3.0 cm to 5.0 cm.

*Stem.*—Shape: Square. Strength: Stiff. Aspect: Upright. Slight bend when bearing flowers. Texture: Very short hairs, hispidulous. Upper parts glabrous. Color: RHS 166A, gray-orange.

Foliage description:

*Arrangement.*—Alternate, heterophyllous.

*Apical leaves.*—Length: 25 to 50 mm. Width: 12 to 20 mm. Overall shape: Lanceolate. Apex shape: Acute. Base shape: Aequilateral. Margin: Serrate.

*Basal leaves.*—Length: 35 to 85 mm. Width: 25 to 67 mm. Overall shape: Cordate. Apex shape: Cuspidate to rounded. Base shape: Cordate. Margin: Crenate.

*Apical & basal leaves.*—

*Texture.*—Smooth, grooved.

*Pubescence.*—Barbellulate, along veins and margin.

*Color.*—Mature: Upper surface: RHS 137A, green; Lower Surface: RHS 138C, green. Immature: Upper surface: RHS 138A, green; Lower Surface: RHS 138C, green.

*Venation.*—Pattern: Reticulate. Color (both surfaces) RHS 138D, green.

*Petiole.*—Arrangement: Angular. Length: Apical: 0 cm. Basal: Range from 3.0 to 6.0 cm. Diameter: 0.4 to 2 mm. Color: RHS 60B, red-purple; blotchy color.

Inflorescence description:

*Flower arrangement and shape.*—Single, large acropetal campanulate flowers in racemes, drooping.

*Natural flowering season.*—Continuous throughout spring and early summer (May through July).

*Time to flower.*—The forcing period depends on the time of year when the plants are moved from outside growing conditions and then subjected to long day photoperiodic treatments indoors. About 9 to 10 weeks, if plants are moved indoors in December or January and subjected to 16 hour long day photoperiodic treatments. About 6 to 7 weeks, if plants are move indoors in April or May and subjected to 16 hour long day photoperiodic treatments.

*Rate of opening.*—About 1 to 5 flowers per week.

*Flower longevity.*—On the plant, flowers last about 5 to 9 days; however, longevity of individual flowers is highly dependent on temperature and light conditions. Flowers persistent.

*Fragrance.*—None.

*Inflorescence size.*—Height: About 10 to 11 cm. Diameter: About 60 to 70 mm.

*Number of flowers per inflorescence.*—1 to 2.

*Number of flowers and buds per lateral stem.*—5 to 6.

*Number of flowers and buds per plant.*—About 30 to 40.

*Buds.*—Length: Up to 30 mm. Diameter: Up to 10 mm. Shape: Oblong, ridged, fluted. Color: Ridges: RHS 59B, red-purple, color blotchy; Valleys: RHS 138D, green.

*Flowers.*—Aspect: Drooping. Shape: Campanulate. Height: About 45 mm. Diameter: About 20 mm. Flowering: Persistent.

*Petals.*—Quantity per flower: 5. Arrangement: Single, sympetalous, campanulate, somewhat gibbous. Appearance: Shiny. Length: Lobes: about 7 mm. Width: Lobes: about 10 mm. Overall Shape: Lobes: triangular. Tip: Acute. Base: Fused. Margin: Entire. Texture: Glabrous. Color (when opening and when fully opened): Inside bell: Ground color: RHS 69C, light red-purple; Dots: RHS 71A, dark red-purple. Outside bell: Ground color: RHS 69A, light red-purple; Dots: RHS 71A, dark red-purple. Fading: No fading, but withers to RHS N187D, gray-purple.

*Sepals.*—Arrangement: Free. Appearance: Shiny. Quantity per flower: 5. Length: About 20 mm. Width: About 5 mm. Overall shape: Hastate, sessile, clasping. Tip: Caudate. Base: Sessile. Margin: Entire. Texture: Glabrous. Color (immature): Upper surface: RHS 138A, green; Under surface: RHS 138C, green. Color (mature): Upper surface: RHS 137A, green; Under surface: RHS 138C, green.

*Peduncles.*—Length: 6 mm to 25 mm. Diameter: About 1 mm. Angle: About 45° to 180°. Strength: Average. Color: RHS 166A, grey-orange.

Reproductive organs:

*Androecium.*—Quantity: 5, adenate to corolla until pollen has been shed. Anther: Shape: Lanceolate, antisepalous, introse, basifixed and two celled. After shedding pollen: curling. Length: About 1 mm. Filament length: about 4 mm. Color: RHS 158B, yellow-white. Pollen: Amount: Moderate. Color: RHS 158B yellow-white.

*Gynoecium.*—Pistil: Quantity: 1. Length: About 14 mm. Stigma: Shape: Tripartite. Color: RHS 155D, white. Style: Length: About 2 mm. Color: RHS 155D, white. Ovary: Color: RHS 150D, yellow-green.

Seed:

*Quantity.*—About 20 to 30 per flower.

*Length.*—About 1 mm.

*Diameter.*—Up to 1 mm.

*Texture.*—Glabrous, hard.

*Color.*—RHS 162A, gray-yellow.

Weather tolerance: Plants of the new *Campanula* have exhibited good tolerance to drought, rain and wind, with low temperature resistance to −20° C.

Disease/pest resistance: 'PKMTAK1' has not been tested.

Disease/pest susceptibility: 'PKMTAK1' has not been tested.

I claim:

1. A new and distinct cultivar of *Campanula* plant named 'PKMTAK1', as illustrated and described herein.

* * * * *